United States Patent
Peterson et al.

(10) Patent No.: US 8,546,625 B2
(45) Date of Patent: Oct. 1, 2013

(54) CONVERSION OF NATURAL PRODUCTS INCLUDING CELLULOSE TO HYDROCARBONS, HYDROGEN AND/OR OTHER RELATED COMPOUNDS

(75) Inventors: Andrew A. Peterson, Copenhagen (DK); Curt R. Fischer, Berkeley, CA (US)

(73) Assignee: Massachusetts Institute of Technology, Cambridge, MA (US)

( * ) Notice: Subject to any disclaimer, the term of this patent is extended or adjusted under 35 U.S.C. 154(b) by 867 days.

(21) Appl. No.: 12/527,714

(22) PCT Filed: Feb. 22, 2008

(86) PCT No.: PCT/US2008/002412
§ 371 (c)(1),
(2), (4) Date: Mar. 1, 2010

(87) PCT Pub. No.: WO2008/103480
PCT Pub. Date: Aug. 28, 2008

(65) Prior Publication Data
US 2010/0228067 A1  Sep. 9, 2010

Related U.S. Application Data

(60) Provisional application No. 60/903,094, filed on Feb. 23, 2007, provisional application No. 61/001,024, filed on Oct. 29, 2007.

(51) Int. Cl.
*C07C 1/00* (2006.01)

(52) U.S. Cl.
USPC ............. 585/240; 585/242; 127/34; 127/42; 127/44; 435/69.1; 435/160

(58) Field of Classification Search
USPC ................. 585/242, 240; 44/605; 568/383; 127/34, 42, 44; 435/41, 69.1, 160
See application file for complete search history.

(56) References Cited

U.S. PATENT DOCUMENTS

| | | | |
|---|---|---|---|
| 3,716,474 A | 2/1973 | Hess et al. | |
| 5,228,982 A | 7/1993 | Scouten et al. | |

(Continued)

FOREIGN PATENT DOCUMENTS

| | | |
|---|---|---|
| JP | 10-130662 A | 5/1998 |
| SE | 7308134-1 | 2/1975 |
| WO | WO 99/29889 A1 | 6/1999 |

OTHER PUBLICATIONS

Cocks, Simon et al. "High-performance liquid chromatography comparison of supercritical-fluid extraction and solvent extraction of microbial fermentation products" Journal of Chromatographys A, 697 (1995) 115-122.

(Continued)

*Primary Examiner* — Nina Bhat
(74) *Attorney, Agent, or Firm* — Wolf, Greenfield & Sacks, P.C.

(57) ABSTRACT

A process for the conversion of sugars and/or other biomass to produce hydrocarbons, hydrogen, and/or other related compounds is described. In one aspect, the process includes fermenting biomass to produce one or more organic intermediates, for example, a carboxylic acid, and optionally, hydrogen. The carboxylic acids may then be decarboxylated to produce carbon dioxide and one or more hydrocarbon compounds. Also described are steps to further react the hydrocarbon compounds to form polymers, hydrocarbon compounds having at least 4 carbon atoms, or the like.

24 Claims, 1 Drawing Sheet

(56) References Cited

U.S. PATENT DOCUMENTS

| | | | |
|---|---|---|---|
| 5,895,506 A | 4/1999 | Cook et al. | |
| 6,180,845 B1* | 1/2001 | Catallo et al. | 585/240 |
| 7,166,753 B2* | 1/2007 | Nakahara et al. | 568/383 |
| 7,816,570 B2* | 10/2010 | Roberts et al. | 585/240 |
| 8,057,666 B2* | 11/2011 | Allan et al. | 210/177 |
| 8,148,579 B2* | 4/2012 | Bradin | 568/387 |
| 8,318,453 B2* | 11/2012 | Medoff | 435/41 |
| 2003/0143659 A1 | 7/2003 | Bijl et al. | |
| 2007/0249029 A1* | 10/2007 | Marshall et al. | 435/161 |
| 2008/0071125 A1* | 3/2008 | Li | 585/361 |
| 2009/0031615 A1* | 2/2009 | Joshi et al. | 44/307 |
| 2009/0093027 A1* | 4/2009 | Balan et al. | 435/99 |

OTHER PUBLICATIONS

Grassie, N. et al. "The Thermal Degradation of Poly(-(D)-β-Hydroxybutyric Acid): Part 3—The Reaction Mechanism" Polymer Degradation and Stability 6 (1984) 127-134.

Grassie, N. et al. "The Thermal Degradation of Poly(-(D)-β-Hydroxybutyric Acid): Part 1—Identification and Quantitative Analysis of Products" Polymer Degradation and Stability 6 (1984) 47-61.

International Search Report and Written Opinion from PCT Application PCT/US2008/002412 dated Aug. 29, 2008.

Kirk-Othmer Encyclopedia of Chemical Technology, vol. 11, pp. 1-55.

Osanai, Yasushi et al. "Enzymatic transformation of aliphatic polyesters into cyclic oligomers using enzyme packed column under continuous flow of supercreitical carbon dioxide with toluene" Science and Technology of Advanced Materials 7 (2006) 202-208.

Savage, Phillip E. et al. "Reactions at Supercritical Conditions: Applications and Fundamentals" AIChE Journal, Jul. 1995, vol. 41, No. 7, pp. 1723-1778.

Vaz Rossel, Carlos Eduardo et al. "Sugar-Based Biorefinery—Technology for Integrated Production of Poly(3-hydroxybutyrate), Sugar, and Ethanol" Biorefineries—Industrial Processes and Products 2006, pp. 209-226.

Watanabe, Masaru et al. "Decomposition of a long chain saturated fatty acid with some additives in hot compressed water" Energy Conversion and Management 47 (2006) 3344-3350.

* cited by examiner

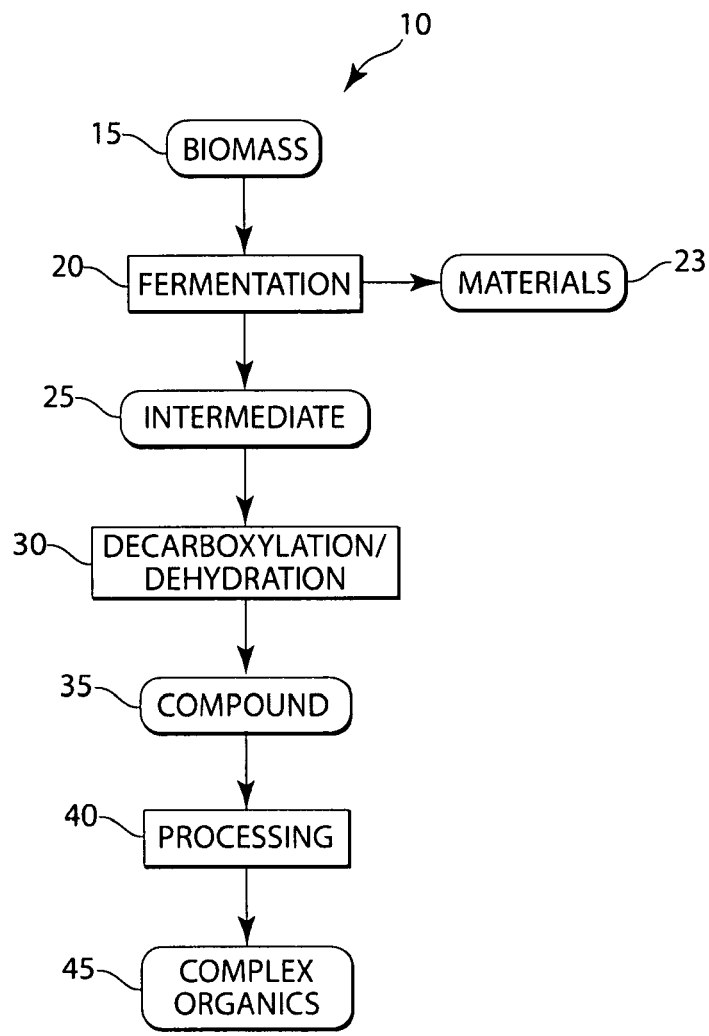

CONVERSION OF NATURAL PRODUCTS INCLUDING CELLULOSE TO HYDROCARBONS, HYDROGEN AND/OR OTHER RELATED COMPOUNDS

RELATED APPLICATIONS

This application is a national-stage application under 35 U.S.C. §371 of International Patent Application Serial No. PCT/US08/002,412, filed Feb. 22, 2008, entitled "Conversion of Natural Products Including Cellulose to Hydrocarbons, Hydrogen, and/or Other Related Compounds," which claims the benefit of U.S. Provisional Patent Application Ser. No. 60/903,094, filed Feb. 23, 2007, entitled "Conversion of Natural Products Including Cellulose to Hydrocarbons, Hydrogen, and/or Other Related Compounds"; and U.S. Provisional Patent Application Ser. No. 61/001,024, filed Oct. 29, 2007, entitled "Conversion of Natural Products Including Cellulose to Hydrocarbons, Hydrogen, and/or Other Related Compounds." Each of these applications is incorporated herein by reference.

FIELD OF INVENTION

The present invention generally relates to the conversion of sugars and/or other biomass to produce hydrocarbons, hydrogen, and/or other related compounds.

BACKGROUND

Due to energy security and environmental benefits, the alternative fuel market has grown to over 500 million gallons per year. Likewise, the overall biofuels market has shown tremendous growth, topping 5 billion gallons per year due to even greater energy security and environmental benefits, in addition to agricultural development advantages. Similarly, the chemicals industry is re-tooling itself to produce many platform chemicals from renewable resources, such as biomass. With domestic federal and state incentives in place to encourage continued alternative fuel and biofuel growth, these markets promise to continue to encompass an increasing share of the 140+ billion gallon gasoline and 40+ billion gallon diesel markets.

Propane is the most widely consumed alternative fuel in the United States, with current total propane demand topping 21 billion gallons per year, driven by residential and commercial (45%), petrochemicals (38%), industrial (7%), farming (7%), and transportation (3%) uses. However, no economic route to renewable propane is currently known. Likewise, the markets for propylene and ethylene, feedstocks for the production of engineering plastics, are estimated to be well in excess of 50 billion tons per annum, each.

SUMMARY OF THE INVENTION

The present invention generally relates to the conversion of sugars and/or other biomass to produce hydrocarbons, hydrogen, and/or other related compounds. The subject matter of the present invention involves, in some cases, interrelated products, alternative solutions to a particular problem, and/or a plurality of different uses of one or more systems and/or articles.

In one aspect, the invention is a method. The method, according to a first set of embodiments, includes acts of fermenting biomass to form an hydrocarbon organic intermediate, and decarboxylating and/or dehydrating the organic intermediate to form a hydrocarbon compound. In some cases, the decarboxylating and/or dehydrating reaction may be performed at a temperature of at least about 475 K and/or a pressure of at least about 1.55 MPa. In another set of embodiments, the method includes acts of fermenting biomass to form a organic intermediate, and exposing the organic intermediate to a supercritical fluid.

The method, in accordance with yet another set of embodiments, includes acts of fermenting the biomass to form an organic intermediate, and exposing the organic intermediate to a temperature of at least about 475 K and a pressure of at least about 1.55 MPa. In still another set of embodiments, the method includes acts of fermenting biomass to form an organic intermediate and water, and without removing the water, reacting the organic intermediate to form a hydrocarbon compound.

In some cases, the organic intermediate may comprise 3 or more carbon atoms. In another aspect, the present invention is directed to a method of making one or more of the embodiments described herein. In another aspect, the present invention is directed to a method of using one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 1 is a flowsheet illustrating one embodiment of the invention.

DETAILED DESCRIPTION

The present invention generally relates to the conversion of sugars and/or other biomass to produce hydrocarbons, hydrogen, and/or other related compounds. In one aspect, the invention includes fermenting biomass to produce one or more organic intermediates, for example, a carboxylic acid, and optionally, hydrogen. The carboxylic acid may then be decarboxylated to produce $CO_2$ and one or more hydrocarbon compounds, for example, an alkane or an alkene, such as propane or ethylene. Such reactions can occur, in some cases, under hydrothermal conditions, and in some instances, without the use of or need for electrolysis of the reactants. In some cases, for example, if the carboxylic acid (or other organic intermediate) includes a hydroxide moiety, the carboxylic acid may be dehydrated, i.e., reacted such that the hydroxide moiety is removed from the molecule as $H_2O$. In certain embodiments, a hydrocarbon compound may then be further reacted to produce other compounds, for example, hydrocarbons having at least 4 carbon atoms (e.g., gasoline), polymers such as polypropylene or polyethylene, or the like. Other aspects of the invention relate to devices for performing such reactions, methods of promoting the making or use of such reactions, or the like.

Referring now to the example illustrated in FIG. 1, in process 10, biomass 15 is first fermented 20, producing intermediate 25, which may be one or more compounds. Examples of intermediates include butyric acid or 3-hydroxybutyrate, as discussed below. In some cases, fermentation 20 also results in materials 23, such as $H_2O$, $CO_2$, $H_2$, etc. These materials may be collected and used in other processes, converted into energy, or the like. Intermediate 25 can then be decarboxylated and/or dehydrated 30 to produce one or more hydrocarbon compounds 35. In some cases, as described in more detail below, this reaction may occur at or near hydrothermal conditions, for example at relatively high temperatures and/or pressures. Optionally, the hydrocarbon compounds may be further processed 40, e.g., to produce more complex hydrocarbons 45 (e.g., having four or more carbon atoms) such as gasoline, polymers such as polyethylene or propylene, or the like. This process will be described in detail below.

In certain aspects of the invention, biomass is used as a starting material. Typically, the biomass is any material derived from a living organism, often plants, and may be purified or, in some cases, used without purification. For example, plants such as corn, sugar cane, sugar beets, trees, straw, rice, or cotton may be harvested, optionally cut or ground into smaller pieces, and used in a fermentation reaction with or without further processing.

In some embodiments, the biomass may be chosen such that it contains a substantial amount of sugars or other carbohydrates, such as glucose, fructose, xylose, maltose, sucrose, galactose, and the like. In some cases, the sugars present may be fermentable, i.e., the sugars can be treated, e.g., as discussed below, to form reduced compounds such as alcohols or carboxylic acids. Often, such fermentation processes may occur in an anaerobic environment, or at least in an environment where oxygen is not the exclusive destination of reducing equivalents produced during the fermentation reaction. In some embodiments, the biomass is chosen such that it is relatively rich in sugars or carbohydrates, which may be present as simple sugars and/or in polymeric form. For instance, glucose can be polymerized to form celluloses or starches. Accordingly, in one embodiment, the biomass may be selected that it contains a substantial amount of cellulose and/or starch. As specific, non-limiting examples, the biomass may contain a substantial amount of switchgrass, wood, or bamboo. In some cases, any amount of sugar (which may include cellulose and/or starches), or other carbohydrates, may be used. For example, the amount of sugar present may be at least about 25%, at least about 50%, at least about 60%, at least about 70%, at least about 75%, at least about 80%, at least about 85%, at least about 85%, at least about 90%, at least about 95%, or substantially all of the total biomass.

An example of a screening test to determine glucose content of a biomass sample involves using acid hydrolysis. Various acid hydrolysis tests are known to those of ordinary skill in the art; in one suitable test, a sample of biomass is hydrolyzed in the presence of a suitable acid, such as trifluoroacetic acid. Such acid hydrolysis breaks down cellulose or starch into soluble monosaccharides, which can then be analyzed using standard techniques such as a phenol-sulfuric acid assay (generally, the sample is reacted with phenol and sulfuric acid, and assayed against known standards), or any number of assays in common use Besides the above materials, virtually any form of biomass may be used with the present invention. Non-limiting examples of biomass that find potential use with the present invention include grains such as corn grain or wheat grain, sugar cane, sugar beets, wood chips, corn stover, wheat straw, rice straw, high-fructose corn syrup, agricultural crop residue, yard waste, sugarcane bagasse, agave bagasse, cotton, paper, paper processing waste, wood, poplar, forest residue, molasses, algae, etc. In some cases, the biomass may be chosen that it can be fermented to form organic intermediates, and/or to form compounds that can be further processed to produce organic intermediates, such as those discussed below.

In addition to the above, in some cases, syngas may be used with some embodiments of the present invention. Syngas is generally a mixture of CO and $H_2$, although other gases may be present, such as $H_2O$, $CO_2$, $O_2$, other hydrocarbons, etc. Syngas may be generated from a carbon source, such as biomass or a fossil fuel (e.g., coal, natural gas, etc.), using any of a variety of techniques, for instance, steam reforming or gasification of a carbon source, or various waste-to-energy (or biomass-to-energy) gasification processes. Techniques such as these for producing syngas are known to those of ordinary skill in the art.

The biomass and/or syngas may be fermented converted biologically or otherwise to produce one or more organic intermediates. Typically, but not always, conversion includes processes involving living cells. However, in some cases, no living cells are used; instead, in such biological conversion reactions, other processes are used to cause conversion of the biomass or syngas. For example, in one set of embodiments, enzymes are used to cause fermentation of the biomass or syngas. In some cases, the enzymes are derived from once-living cells. Typically, the "organic intermediate" is given its ordinary meaning as used in the art, e.g., a molecule (or molecules) containing carbon and hydrogen, and often contains other heteroatoms such as oxygen or nitrogen. Often, the organic intermediate will contain two or more carbon atoms. Other intermediates can also be formed as well during fermentation, such as $H_2O$, $H_2$, $CO_2$, or CO.

Depending on the fermentation reaction (or other biological conversion reaction), there may be a substantial amount of a single type of organic intermediate produced, or there may be a plurality of different intermediates produced. In some cases, only partial fermentation is desired, i.e., the reaction is allowed to proceed such that a substantial amount of the organic intermediate each comprise at least two carbon atoms, instead of allowing the reaction to proceed to single-carbon compounds such as CO, $CO_2$, or $CH_4$. For instance, after the reaction, at least about 25% of the organic intermediates, at least about 50% of the organic intermediates, at least about 60% of the organic intermediates, at least about 70% of the organic intermediates, at least about 80% of the organic intermediates, at least about 90% of the organic intermediates, or substantially all of the organic intermediates may be present as compounds having two or more carbon atoms, three or more carbon atoms, four or more carbon atoms, etc. Examples of such organic intermediates include, but are not limited to, ethanol, butyric acid, 3-hydroxybutyrate, lactic acid, citric acid, succinic acid, malic acid, acetic acid, propionic acid, oxaloacetic acid, hydroxyalkanoates, or the like.

In one set of embodiments, a biological conversion process is chosen such that the biomass or syngas is reacted to form a carboxylic acid, and in some cases, such that a substantial portion of the biomass or syngas forms carboxylic acids. For instance, the biomass or syngas may be reacted to form carboxylic acids such as acetic acid, butyric acid, lactic acid, citric acid, succinic acid, malic acid, oxaloacetic acid, propionic acid, itaconic acid, gluconic acid 3-hydroxybutyric acid, or the like, and/or salts thereof, for instance, sodium or potassium salts of any of these acids. Other salts, e.g., using any alkali metal or alkaline earth, may also be formed. The biomass or syngas may also be reacted, in some embodiments, to form polymers of these and/or other compounds. For example, the biomass or syngas may be reacted to form a polymeric species such as polyhydroxybutyrate (PHB) or polylactic acid (PLA). In some cases, biological conversion of the biomass or syngas is allowed to proceed such that substantially all of the biomass or syngas forms carboxylic acids. Those of ordinary skill in the art will be aware of fermentation and other biological conversion reactions able to produce carboxylic acids. Non-limiting examples of suitable fermentation processes include production of butyric acid by *Clostridium acetobutylicum* or *Clostridium tyrobutyricum*; the production of lactic acid by *Lactobacillus acidophilus* or *Lactococus lactis*; the production of 3-hydroxybutyric acids or polyesters thereof by *Alcaligenes eutrophus*, recombinant *Escherichia coli*, or other species; the fermentation of succinic acid in *Mannheimia succiniciproducens* or other species, including recombinant species, etc. Other examples of suitable fermentation processes are discussed in the Kirk-Othmer *Encyclopedia of Chemical Technology* (5$^{th}$ Edition, Wiley).

In some embodiments, the biological conversion process may result in the production of other materials, such as $H_2$, $H_2O$, $CO_2$, or the like. In some cases, these materials are gaseous and can be separated from the biomass using routine separation techniques. These materials may be discharged to the environment, treated before being discharged, collected or stored, used in other processes, converted into energy, or the like. For instance, in some cases, hydrogen ($H_2$) may be produced during fermentation as a byproduct gas. The hydrogen may be captured or otherwise separated from the organic intermediate or the fermenting biomass. For instance, the hydrogen gas may be separated and isolated (e.g., stored for later use, such as an energy source), reacted in subsequent reactions (e.g., to form fertilizer or ammonia, for instance, using Haber-Bosch synthesis), and/or routed to devices that can use hydrogen, for example, for use in chemical synthesis, to be oxidized in a fuel cell to produce energy and water, etc.

The organic intermediate(s) may optionally be separated or purified from the fermented biomass. Any suitable technique known to those of ordinary skill in the art may be used to purify the organic intermediate from the fermented biomass or syngas. Non-limiting examples of suitable separation techniques include centrifugation, distillation, filtration, sedimentation, or the like. Such separation techniques are well-known to those of ordinary skill in the art. However, in other embodiments, the organic intermediate is not separated from the fermented biomass or syngas. For example, in some fermentation processes, a large amount of water may be used, and carboxylic acids or other organic intermediates may be contained within the water (e.g., dissolved). Instead of separating the organic intermediates, which may be energy-intensive in some cases, the water may be used in subsequent process steps as discussed below, e.g., within a hydrothermal process. Accordingly, one feature of certain embodiments of the invention is that the organic intermediate produced during fermentation of the biomass or syngas is not separated from any water in the fermentation process.

In some aspects of the invention, the organic intermediate may be decarboxylated and/or dehydrated, using any suitable process conditions to cause decarboxylation and/or dehydration of some or all of the organic intermediate. In certain embodiments, the reaction may produce alkanes and/or alkenes, typically having two or more carbon atoms, and in some cases, substantially all of the organic intermediate is converted into alkanes and/or alkenes. For instance, in certain instances, after decarboxylation and/or dehydration, at least about 25%, at least about 50%, at least about 60%, at least about 70%, at least about 75%, at least about 80%, at least about 85%, at least about 90%, at least about 95%, or substantially all of the organic intermediate is reacted to form alkanes and/or alkenes having two or more carbon atoms. In contrast, in many prior art reactions, only single-carbon molecules are produced (e.g., $CH_4$, $CO_2$, etc.).

Typically, a "decarboxylation" process involves the reaction of an intermediate to produce $CO_2$. For example, with respect to a carboxylic acid, RCOOH, the decarboxylation reaction may proceed reductively and result in the production of RH and $CO_2$, e.g.:

$$RCOOH \rightarrow RH + CO_2.$$

In other cases, the reaction may proceed oxidatively and result in the production of an unsaturated or partially oxidized derivative of R. Thus, for instance, if R is an alkyl group, the reductive reaction may result in the formation of an alkane. Of course, R is not limited to an alkyl group, but can be any suitable organic moiety. For example, R can contain other substituents in other embodiments of the invention, e.g., heteroatoms, carbon-carbon double bonds or carbon-carbon triple bonds, other functional groups (including hydroxides or other carboxylic acid moieties), etc. Specific examples of carboxylic acids that can be decarboxylated include, but are not limited to, acetic acid, butyric acid, lactic acid, citric acid, succinic acid, malic acid, oxaloacetic acid, propionic acid, itaconic acid, gluconic acid, 3-hydroxybutyric acid, or the like. Organic compounds from which a carboxylic acid is easily derived, for example, esters, can also be decarboxylated in some embodiments of the invention, for example, if they are first subject to treatments which liberates free carboxylic acids.

In some embodiments, a catalyst may be used with the decarboxylation reaction. Non-limiting examples of suitable catalysts include bases (for example, mineral bases such as KOH or NaOH, or other bases such as dissolved ammonia), oxidizing agents such as hydrogen peroxide, reducing agents such as hydrogen (optionally, arising from the fermentation reaction, as discussed above), metal catalysts (for example, iron, nickel, platinum, palladium, copper), zeolites, acid catalysts (for example, hydrochloric acid, sulfuric acid, dissolved carbon dioxide, etc.), or metal ion catalysts (for example, copper ions). In other embodiments, however, no catalyst is needed and the reaction can occur without the presence of a catalyst.

A typical "dehydration" process involves the removal of a hydroxide from an intermediate to produce $H_2O$. The hydroxide may combine with a hydrogen atom from another carbon atom in the molecule (often, attached to an adjacent carbon atom), causing formation and release of $H_2O$, and often, the formation of a double bond within the molecule, e.g.:

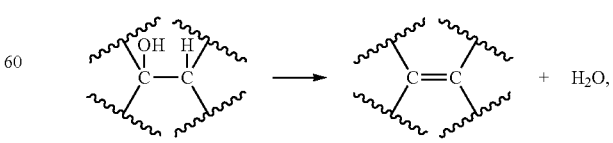

where ⟟ in the above structures indicates attachment of any suitable moiety (e.g., hydrogen, an alkyl, other functional groups, etc.). Accordingly, alkene compounds, or other compounds containing carbon-carbon double bonds, can be produced in various embodiments of the invention. As a specific, non-limiting example, hydroxybutyric acid ($CH_2OH—CH_2—CH_2—COOH$) may be dehydrated to produce but-3-enoic acid ($CH_2=CH—CH_2—COOH$) (which may, in some cases, subsequently be decarboxylated to yield propylene, $CH_2=CH—CH_3$).

As mentioned, in some cases, both decarboxylating and dehydrating reactions may occur, and these reactions can occur in any order. For instance, lactic acid ($CH_3—CHOH—COOH$) may be both decarboxylated and dehydrated to produce ethylene ($CH_2=CH_2$). Other non-limiting examples of suitable reactions include reacting butyric acid to produce propane, reacting a hydroxybutyric acid or a polyester thereof to produce propylene, reacting a polyester of lactic acid to produce ethylene, reacting citric acid to produce propylene, reacting malic acid to produce ethylene, reacting succinic acid to produce ethane and/or propionic acid, reacting fumaric acid to produce acetylene and/or ethylene, reacting acetic acid to produce methane, reacting propionic acid to produce ethane, or reacting 3-hydroxypropionic acid to produce ethylene. In some embodiments, the organic intermediate may include more than one of these species, and/or other species, and thus, more than one of these reactions and/or other processes may occur during the decarboxylation or dehydration reactions. In one set of embodiments, salts of any of the species described above may be used. For instance, a salt of a carboxylic acid may be reacted in similar fashion as above (e.g., potassium butyrate instead of butyric acid may be used).

In one set of embodiments, the above-described decarboxylating and/or dehydrating reactions occur under generally hydrothermal conditions, i.e., at relatively high temperatures and/or pressures. In some embodiments, the temperature of the reaction may be at least about 400 K, at least about 425 K, at least about 450 K, at least about 475 K, at least about 500 K, at least about 525 K, at least about 550 K, at least about 575 K, or at least about 600 K, and/or the pressure may be at least about 6 MPa, at least about 8 MPa, at least about 10 MPa, at least about 12 MPa, at least about 14 MPa, at least about 16 MPa, at least about 18 MPa, or at least about 20 MPa.

In some embodiments, the decarboxylating and/or dehydrating reactions may occur in the presence of a fluid that is at or near supercritical. Those of ordinary skill in the art will be aware of supercritical fluids, and techniques for identifying the same. For instance, the reaction can occur, in one embodiment, at or near conditions in which water is supercritical, i.e., at temperatures greater than about 647 K and pressures greater than about 22 MPa. In some cases, the reaction occurs at supercritical conditions (above the critical temperature and pressure), but in other cases, the reaction may occur under subcritical conditions (i.e., where the temperature and pressure are not both supercritical, and one or both are below their respective critical points). For example, the temperature may be within about 10 K, within about 20 K, within about 30 K, within about 40 K, or within about 50 K of the critical temperature, and/or the pressure may be within about 1 MPa, within about 2 MPa, within about 3 MPa, within about 4 MPa, or within about 5 MPa of the critical pressure. Supercritical conditions may be desirable in some cases, as that may encourage free radical formation and reaction; however, in other cases, subcritical conditions may be desirable, as that may encourage ionic reactions to occur. Non-limiting examples of supercritical fluids that are potentially suitable for use with the present invention include $H_2O$, $CO_2$, methane, ethane, propane, ethylene, propylene, methanol, ethanol, or acetone.

The term "supercritical fluid" defines a physical state of a particular species that exists above that particular species' critical point. The critical point of a species is that point on an equilibrium diagram at the intersection of the critical temperature and critical pressure of the species. The critical temperature of a species is defined by the minimum temperature above which two distinct phases of the fluid (liquid and vapor) cannot coexist, at any pressure. The critical pressure is the vapor pressure of the species at its critical temperature. Thus, a supercritical fluid is defined as a phase existing above the critical temperature and above the critical pressure of a particular species. Supercritical fluids exhibit unusual characteristics different from certain characteristics exhibited by liquids, solids, or gases. In many aspects, supercritical fluid properties are quite distinct from the subcritical liquid-phase properties and the subcritical gas-phase properties of the same fluid.

A simple screening test for determining suitable operating conditions for a given organic intermediate in a hydrothermal reaction is to prepare a batch reactor containing the intermediate and water that can be heated and pressurized such that the water reaches the critical point, then systematically vary the temperature and pressure near the critical point (in both positive and negative directions) until a desired amount of reactivity is reached. In some cases, the pressure may be effectively varied or controlled by controlling the mass of water fed to this batch reactor. Any suitable method, for example, gas chromatography, can be used to monitor the reaction products. An experiment using this technique is given in the Examples section, below. It should be noted that too much reactivity may result in the formation of excessive amounts of one-carbon species, i.e., due to excessive fragmentation of alkanes, alkenes, or the like during the reaction.

In some aspects, the hydrocarbon compound may be further reacted, for example, to produce more complex hydrocarbon compounds (e.g., having 4, 5, 6, or more carbon atoms), and/or to produce polymers such as polypropylene, polyethylene, etc. Any of the above-described hydrocarbon compounds can be reacted, alone or in combination with each other. Any suitable reaction involving hydrocarbon compounds such as alkanes and/or alkenes, such as propane or ethylene, may be used. Thus, for example, a hydrocarbon compound produced using any of the above-described methods may further be reacted to form a polymer, or to produce a hydrocarbon having at least 4 carbon atoms, etc.

For example, in one set of embodiments, the hydrocarbon compound may be reacted to produce gasoline or other fuel oils, for instance, kerosene, diesel, heating oil, or the like, using techniques known to those of ordinary skill in the art. For instance, propylene may be dimerized to form gasoline, or propylene and isobutane may be reacted (e.g., in an "alkylation" reaction) to form a fuel. Non-limiting examples of such reactions are disclosed in Abdullah M. Aitani, "Oil Refining and Products," in *Encyclopedia of Energy*, Vol. 4 (Elsevier, 2004). In some reactions, the hydrocarbon compounds may include ethane, ethylene, propane, and/or propylene.

In another set of embodiments, the hydrocarbon compounds may be polymerized. Techniques for polymerizing alkanes and/or alkenes are well-known to those of ordinary skill in the art. For example, ethylene may be polymerized to produce polyethylene, propylene may be polymerized to produce polypropylene, etc. A non-limiting example of a suitable polymerization processes is Ziegler-Natta polymerization.

The following applications are incorporated by reference herein: U.S. Provisional Patent Application Ser. No. 60/903,094, filed Feb. 23, 2007, entitled "Conversion of Natural Products Including Cellulose to Hydrocarbons, Hydrogen, and/or Other Related Compounds"; and U.S. Provisional Patent Application Ser. No. 61/001,024, filed Oct. 29, 2007, entitled "Conversion of Natural Products Including Cellulose to Hydrocarbons, Hydrogen, and/or Other Related Compounds."

The following examples are intended to illustrate certain embodiments of the present invention, but do not exemplify the full scope of the invention.

Example 1

In this example, biologically derived polyhydroxybutyrate ("PHB"), at 1 wt % in water, was reacted in a batch reactor that was exposed to a 400° C. sandbath for 20 minutes, before being quenched. Macroscopic quantities of propylene were recorded, and about 20% of the headspace gases were propylene, as determined by GC (gas chromatography) analysis. The reaction was designed to have a density of about 300 kg/m$^3$ and a pressure of about 285 bar. Estimates of the yield of propylene on PHB charged revealed that up to about 47% of the PHB may have been converted selectively to propylene. The propylene yield on PHB consumed was higher, however, because visual inspection revealed that the liquid phase in the reactor after re-cooling was milky and turbid, indicating that some solid, unconsumed PHB polymer remained suspended in this phase.

At the time of the experiments, standards of $C_1$-$C_6$ paraffins and $C_2$-$C_6$ olefins had just been purchased and run to get one point calibrations, but calibration curves have not been entered into the GC method; thus, chemical names on the chromatograms do not necessarily align to the chemicals noted. The sampling port was flushed with atmospheric air 10 minutes before the experiments.

For these experiments, a reactor was assembled out of 316SS HIP fittings with a (roughly) measured internal volume of 25.5 mL. To this reactor, 0.08 g of PHB and 7.65 g of water were added, which were calculated to give a density of 300 kg/m$^3$ and a pressure of 285 bar at 400° C. Calculations showed that there would be about 5 mmoles of $O_2$ in the reactor, which should not be enough to oxidize a significant portion of the PHB charged to the reactor.

The reactor was placed in a 400° C. sandbath for 20 minutes. The top part of the reactor was extending out of the sandbath, so the vessel was not isothermal and these data are not necessarily quantitatively accurate. After 20 minutes, power was cut to the sandbath and after about 7 more minutes, the sandbath had cooled to 350° C., at which point it was deemed safe to enter and place the reactor into a water bath to quench the reaction. After about 20 minutes of quenching in 16° C. water, a known-volume chamber was attached to the top of the reactor and the valve opened. The gauge pressure of the chamber raised to 10 psi$_g$ when the valve was opened. Note that the bottom part of the reactor, at this point, was in the 16° C. water and the top part was in the air, which was about 25° C. A sample was quickly taken from the sampling port and injected into the GC. 125 microliters were injected into the GC. The valve connecting the reactor and the known volume chamber was quickly closed to prevent back mixing.

After about 30 minutes, the top (small) nut was removed from the reactor and another gas sample was quickly taken from the headspace and injected on the GC. The liquid was decanted into a graduated cylinder and measured to be about 7 mL, indicative of no major leaks. This water was saved for HPLC analysis for PHB, 3-hydroxybutyrate (3hb), and crotonic acid.

HPLC analysis revealed the presence of significant amounts of crotonic acid, but little amounts of 3-hydroxybutyric acid, indicating that dehydration of the free acid was comparatively rapid at the conditions tested.

Yield was estimated with the following data:

TABLE 1

| |
|---|
| 0.08 g PHB reactor charge |
| 86.161 PHB FW, monomer basis |
| 0.928494 mmol PHB monomer equivalent |
| 25.5 mL reactor volume |
| 10 psi$_g$ internal pressure after reaction |
| 26.4 microliters volume of propylene in GC sample |
| 125 microliters volume of GC sample |
| 0.2112 volume fraction (or mole fraction) of propylene in GC sample |
| 50 mL volume of upper chamber |
| 75.5 mL volume of whole system which was pressurized to 10 psig |
| 0.0821 mL atm/mmol K gas constant |
| 1.20687 mL psia/mmol K gas constant |
| 298 K approximate temperature |
| 2.09927917 mmol total ideal gas inside reactor |
| 0.44336776 mmol propylene inside reactor |
| 47.75% mol/mol yield of polypropylene on PHB charged |

Example 2

This example describes the production of potassium butyrate in a CSTR (Continuously Stirred Tank Reactor) at 425° C. Butyric acid at 20 g/L, buffered to a of about pH 8 with potassium hydroxide, was run in a CSTR at 5 mL/min. A high gas flow rate was observed, and the two dominant species observed were propane and propylene, as observed by residence time on GC (gas chromatography). Results showed yields on the order of 5% for propane, although equipment conditions precluded precise determination of yields, etc. in this example. During the run, the temperature varied somewhat between 415° C. and 441° C.

Table 2 shows gas flow rates were observed, as measured with an inverted graduated cylinder and a stopwatch. Times are as recorded; if no time is noted, then multiple flow rates were taken consecutively. Table 3 illustrates gas compositions as were measured by GC. Percentages are volume percent.

TABLE 2

| Clock time | Flow rate (mL/min) |
|---|---|
| 17:31 | 1.40 |
| 17:47 | 4.29 |
| 17:51 | 5.01 |
|  | 3.41 |
| 18:24 | 2.90 |
| 18:32 | 3.61 |
| 18:41 | 6.84 |
|  | 8.66 |
|  | 8.89 |
| 18:50 | 3.54 |
| Average | 4.86 |
| Standard Deviation | 2.50 |

TABLE 3

| Clock time | Methane | Ethane | Ethylene | Propane | Propylene | Butane |
|---|---|---|---|---|---|---|
| 17:15 | 10.5% | 0.4% | 2.5% | 15.8% | 15.0% | 0.00% |
| 17:48 | 14.2% | 0.7% | 3.1% | 37.1% | 21.4% | 0.02% |
| 18:31 | 9.7% | 0.3% | 1.4% | 29.8% | 16.3% | 0.01% |
| 18:55 | 10.9% | 0.3% | 1.3% | 33.8% | 19.9% | 0.01% |
| Average | 11.3% | 0.4% | 2.1% | 29.1% | 18.2% | 0.01% |

Taking the averages from Tables 1 and 2 as estimates potentially lacking in precision, the flow rate of propane out of the reactor was 2.55 mg/min and of propylene was 1.52 mg/min. Compare this to the feed flowrate of butyric acid of 100 mg/min; which if it was converted 100% to propane would result in 50.05 mg/min of propane produced. Table 4 summarizes these average "yields," on a mass basis normalized to the amount of propane that would come out of the reactor if all of the butyric acid were converted to propane.

TABLE 4

| Component | "Average" mass flow rate, mg/min | "Average" yield |
|---|---|---|
| Propane | 2.55 | 5.1% |
| Propylene | 1.52 | 3.0% |
| Methane | 0.36 | 0.7% |
| Ethane | 0.02 | 0.05% |
| Ethylene | 0.11 | 0.23% |
| Butane | 0.0014 | 0.0028% |

Equipment conditions precluded precise determination of yield in this example; yields are best estimates. The composition of the liquid effluent was not determined, so the amount of butyric acid that was unreacted is not known.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
   fermenting biomass or converting syngas to form an organic intermediate, at least about 25% of the organic intermediate comprising at least 3 carbon atoms; and
   decarboxylating or dehydrating the organic intermediate to form a hydrocarbon compound at a temperature of at least about 475 K or a pressure of at least about 1 MPa or both.

2. The method of claim 1, wherein the organic intermediate comprises butyric acid.

3. The method of claim 1, wherein the organic intermediate comprises polyhydroxybutyrate.

4. The method of claim 1, wherein at least about 25% of the organic intermediate comprises at least 4 carbon atoms.

5. The method of claim 1, wherein the organic intermediate comprises a carboxylic acid.

6. The method of claim 1, wherein the hydrocarbon compound comprises alkanes or alkenes or both.

7. The method of claim 1, wherein the act of fermenting comprises fermenting to form an organic intermediate and hydrogen gas.

8. The method of claim 1, comprising decarboxylating or dehydrating the organic intermediate using a catalyst.

9. The method of claim 1, wherein the act of decarboxylating or dehydrating the organic intermediate occurs under conditions in which water is supercritical.

10. The method of claim 1, wherein the biomass comprises a material having at least about 25% fermentable sugar.

11. The method of claim 1, wherein the biomass comprises one or more of corn grain, sugar cane, sugar beets, sugar, glucose, wood chips, corn stover, wheat straw, rice straw, high-fructose corn syrup, agricultural crop residue, yard waste, sugarcane bagasse, agave bagasse, cotton, paper, paper processing waste, wood, poplar, forest residue, or molasses.

12. The method of claim 1, wherein the biomass comprises algae.

13. The method of claim 1, wherein the hydrocarbon compound comprises propane.

14. The method of claim 1, wherein the hydrocarbon compound comprises propylene.

15. The method of claim 1, further comprising reacting the hydrocarbon compound to form a polymer.

16. The method of claim 1, further comprising reacting the hydrocarbon compound to form gasoline.

17. A method, comprising:
    fermenting biomass or converting syngas to form an organic intermediate, at least about 25% of the organic intermediate comprising at least 3 carbon atoms; and
    exposing the organic intermediate to a supercritical fluid.

18. The method of claim 17, wherein the organic intermediate comprises a polyester formed from condensation polymerization of a beta-hydroxy carboxylic acid to form a poly(beta-hydroxy alkanoate).

19. A method, comprising:
    fermenting biomass or converting syngas to form an organic intermediate in water, at least about 25% of the organic intermediate comprising at least 3 carbon atoms; and
    without removing the water, reacting the organic intermediate to form a hydrocarbon compound.

20. The method of claim 1, comprising fermenting biomass and converting syngas to form the organic intermediate.

21. The method of claim 1, comprising decarboxylating and dehydrating the organic intermediate.

22. The method of claim 1, comprising decarboxylating or dehydrating the organic intermediate to form a hydrocarbon compound at a temperature of at least about 475 K and a pressure of at least about 1 MPa.

23. The method of claim 17, comprising fermenting biomass and converting syngas to form the organic intermediate.

24. The method of claim 19, comprising fermenting biomass and converting syngas to form the organic intermediate.

* * * * *